United States Patent
Pastuhov et al.

(10) Patent No.: US 10,758,172 B2
(45) Date of Patent: Sep. 1, 2020

(54) METHOD AND SYSTEM OF MULTI-PARAMETER EVALUATION OF THE EFFECT OF THE ENVIRONMENT ON A PERSON

(71) Applicant: Boris Ivanovich Pastuhov, Moscow (RU)

(72) Inventors: Boris Ivanovich Pastuhov, Moscow (RU); Vladimir Andreevich Didenko, Moscow (RU); Igor' Vladimirovich Parafeynikov, Korolev (RU)

(73) Assignee: Boris Ivanovich Pastuhov, Moscow (RU)

( * ) Notice: Subject to any disclaimer, the term of this patent is extended or adjusted under 35 U.S.C. 154(b) by 186 days.

(21) Appl. No.: 15/781,682

(22) PCT Filed: Nov. 3, 2016

(86) PCT No.: PCT/RU2016/000748
§ 371 (c)(1),
(2) Date: Jun. 5, 2018

(87) PCT Pub. No.: WO2018/030912
PCT Pub. Date: Feb. 15, 2018

(65) Prior Publication Data
US 2018/0344238 A1 Dec. 6, 2018

(30) Foreign Application Priority Data

Aug. 10, 2016 (RU) ................................. 2016133025

(51) Int. Cl.
*A61B 5/00* (2006.01)
*H04W 4/02* (2018.01)
*G06Q 50/22* (2018.01)
*A61B 5/02* (2006.01)
*A61B 5/08* (2006.01)
*A61B 5/117* (2016.01)
*G01W 1/00* (2006.01)

(52) U.S. Cl.
CPC .................. *A61B 5/48* (2013.01); *A61B 5/00* (2013.01); *A61B 5/02* (2013.01); *A61B 5/08* (2013.01); *A61B 5/117* (2013.01); *A61B 5/42* (2013.01); *A61B 5/4306* (2013.01); *A61B 5/4528* (2013.01); *G01W 1/00* (2013.01); *G06Q 50/22* (2013.01); *H04W 4/025* (2013.01); *G01W 2203/00* (2013.01)

(58) Field of Classification Search
CPC .... A61B 5/48; A61B 5/00; A61B 5/02; A61B 5/08; A61B 5/117; A61B 5/42; A61B 5/4306; A61B 5/4528; G06Q 50/22; G01W 1/00; G01W 2203/00; H04W 4/025; H04L 9/3236

See application file for complete search history.

(56) References Cited

U.S. PATENT DOCUMENTS

| | | | |
|---|---|---|---|
| 7,109,913 B1* | 9/2006 | Paramore | G01C 23/00 342/26 B |
| 2001/0034839 A1* | 10/2001 | Karjoth | H04L 9/3236 713/190 |
| 2008/0021288 A1* | 1/2008 | Bowman | H04L 67/18 600/300 |
| 2008/0207183 A1* | 8/2008 | Root | H04L 67/306 455/414.2 |
| 2014/0316220 A1* | 10/2014 | Sheldon | A61B 5/0205 600/301 |
| 2016/0012748 A1* | 1/2016 | Donavon | G09B 5/02 434/225 |
| 2016/0091474 A1* | 3/2016 | Griffon | G01N 33/0036 702/24 |
| 2017/0039344 A1* | 2/2017 | Bitran | G06F 19/3475 |
| 2017/0259072 A1* | 9/2017 | Newham | A61N 1/37252 |
| 2019/0183780 A1* | 6/2019 | Pan | A61K 8/466 |

FOREIGN PATENT DOCUMENTS

JP 2016148517 A 8/2016
RU 25991 U1 10/2002

OTHER PUBLICATIONS

Sevostyanova et al., "Pathological Reacting to Meteorological Changes as a Risk-Factor of Cardio-Vascular Pathology in the North", Clinical Medical Research, vol. 2, No. 4, 2013, pp. 53-57. (Year: 2013).*

* cited by examiner

*Primary Examiner* — Catherine M Voorhees
(74) *Attorney, Agent, or Firm* — Craft Chu PLLC; Andrew W. Chu

(57) ABSTRACT

The method and system for evaluating the effect of weather, geomagnetic background and the air on the condition of a person's body—involves the input of personal data—by a computer device user; the determination or specification of a geolocation; the transmission of the personal data and the geolocation data, to a processing unit; the requesting of environmental forecast data from a weather server; the transmission of the forecast data; the transmission of the user and forecast data to an encoder and the generation of a single hash code; the transmission of the hash code to a decoder and the correlation with a database of dependencies of the functioning of human body systems on weather, geomagnetic background and air condition parameters; and the transmission of the correlated data to a display—and the display of information about the effect of environmental parameters on the functioning of human body systems.

12 Claims, 1 Drawing Sheet

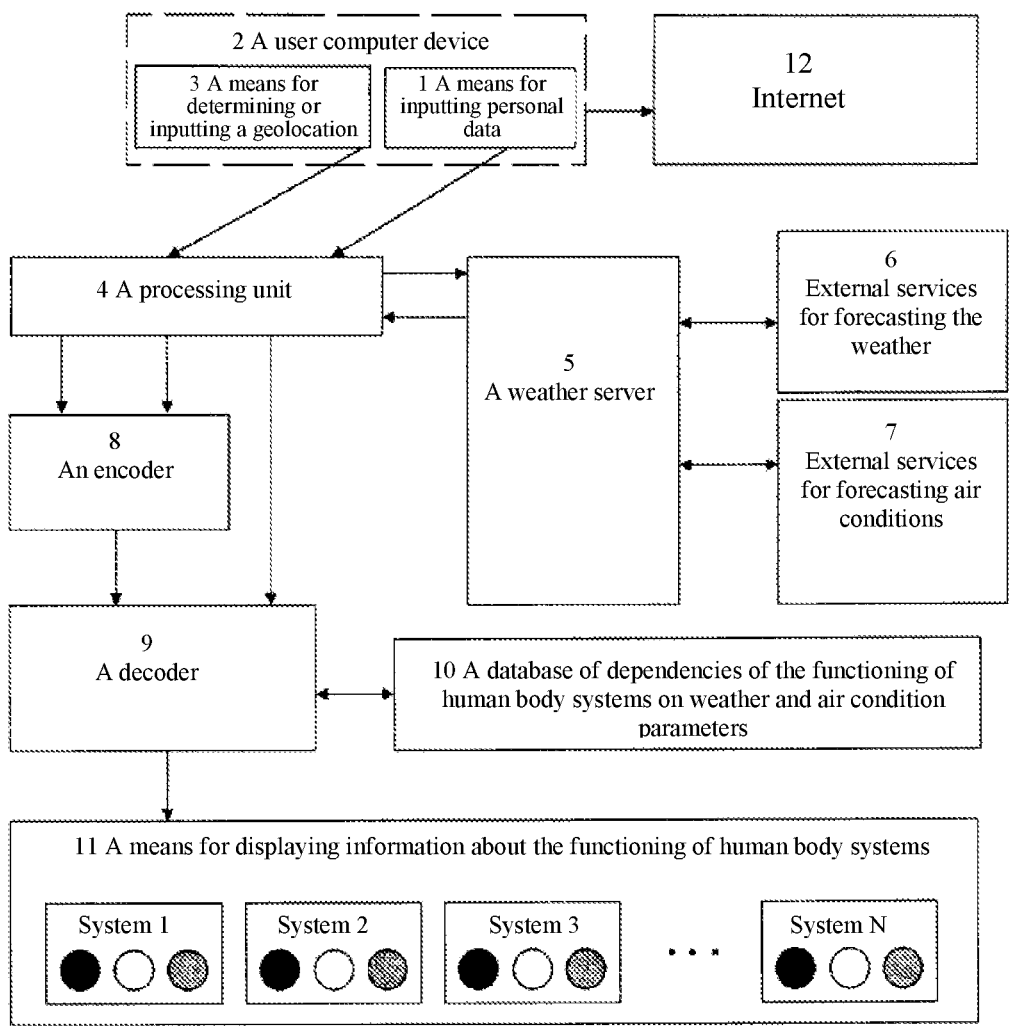

METHOD AND SYSTEM OF MULTI-PARAMETER EVALUATION OF THE EFFECT OF THE ENVIRONMENT ON A PERSON

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.
STATEMENT REGARDING PRIOR DISCLOSURES BY THE INVENTOR OR A JOINT INVENTOR
Not applicable.

BACKGROUND OF THE INVENTION

1. Field of the Invention

The invention relates to computing systems for predicting the condition of a person depending on environmental parameters, and more particularly to a method and system for evaluating the effect of weather, Earth's magnetic field (the geomagnetic background) and the air quality on the condition of a person's body (a computer device user).

2. Description of Related Art Including Information Disclosed Under 37 CFR 1.97 and 37 CFR 1.98.

The closest analog of the claimed invention is an information system and method for notifying users about the effect of environment on the user health disclosed in the Patent of Japan JP59145988, Nov. 5, 2016. This system includes: an information server comprising information about preceding ambulance calls and meteorological conditions, and configured to map the provided information with a database storing information about meteorological conditions and diseases; a data unit adapted to receive information about the environment at a user location; a generator accessing the database and obtaining information about the environment for each user, and a device transmitting information about a user disease. The data unit receives environmental data from news agencies. The generator generates the relevant information about an environmental effect on a person's body by comparing data about the meteorological conditions and diseases.

The drawback of this solution is in relatively poor possibilities since this solution uses only weather parameters. The analogous solution uses a degree of person's meteosensitivity, geomagnetic background, air quality and data about the presence of allergenic pollen in the air. In addition, the analogous solution doesn't provide with information about risks related to a cardiovascular system, food allergy, allergic rhinitis and a human musculoskeletal system.

Moreover, this solution doesn't provide a specific system operation algorithm. The system configuration described above doesn't enable processing multiple environmental parameters (only individual weather parameters are considered) and person's health factors including personal information and user location per operation, thus, complicating and slowing down the system operation. For instance, processing a request for a user having several health problems will take more time than in the case of a single problem. In addition, the more health problems a user has the more time is needed for cyclic processing.

BRIEF SUMMARY OF THE INVENTION

It is an object of the present invention to enhance a therapeutic and preventive efficiency by informing a user about a likely effect of current and forecast weather parameters, geomagnetic background, and air quality on the functioning of different human body systems according to a degree of their meteosensitivity.

The technical result provided by the present invention is in an improved objectivity of forecast data, an improved system operating speed, a simplified configuration of the said system and an improved potential thereof as a result of the integration of different weather parameters, a geomagnetic background, and air quality.

Said technical result is achieved by the claimed method for multi-parameter evaluating an effect of environmental parameters on the functioning of human body systems by that it comprises inputting by a computer device user personal data which include at least gender and age, a degree of the meteosensitivity and a list of medical problems of a user, determining or specifying by said computer device user a geolocation, transmitting the user data containing personal and geolocation data to a processing unit, requesting by the processing unit the current and forecast environmental data from a weather server, wherein said data include forecast data about a weather, geomagnetic background and air condition according to the geolocation, a transmission of the forecast data to the processing unit by the weather server, transmitting the user and forecast data to an encoder and generating a single hash code containing the user and forecast data, transmitting the hash code to a decoder and correlating said code with a database of dependencies of a functioning of human body systems on weather, geomagnetic background and air condition parameters, transmitting the correlated data to a displaying means and displaying information about the effect of environmental parameters on the functioning of human body systems.

Said technical result is achieved by a system of multi-parameter evaluation of the effect of environmental parameters on a functioning of human body systems by that it comprises: a means for inputting personal data of a computer device user, said data includes at least gender and age, a means for determining or inputting a geolocation of the computer device user, a processing unit configured to communicate with a user computer device and receive a user data therefrom, said data includes personal and geolocation data, a weather server connected to a processing unit, external services for forecasting weather, geomagnetic background and air condition connected to the weather server so as to transmit environmental forecast data to the processing unit, said data includes forecast data about a weather, geomagnetic background and air condition according to a user geolocation, an encoder connected to the processing unit and configured to generate a single hash code comprising user and forecast data, a decoder connected to the encoder and configured to correlate the hash code with a database of dependencies of functioning of human body systems on environmental parameters, a database of dependencies connected to the decoder and containing a hash table of dependencies of the functioning of human body systems on weather, geomagnetic background and air condition parameters, and a means for displaying information about an effect of environmental parameters on the functioning of human body systems.

Furthermore, there are particular embodiments of the invention envisaged according to which:

- a user geolocation is determined by means of a navigation module of a computer device,
- user personal data is inputted by means of a computer device interface, wherein the user further inputs a degree of the meteosensitivity as the personal data,
- an air temperature, atmospheric pressure, air humidity, wind direction and power, precipitation type and intensity, atmospheric pressure dynamics for 12 hours and an ultraviolet index are used as weather forecast data,
- a background air pollution and presence of allergenic pollen in the air are used as forecast data about air condition,
- following disease groups are used as factors reflecting the functioning of the body systems: enhanced emotional lability, neurosis; acute respiratory diseases; tonsillitis, aggravation of chronic tonsillitis; acute pneumonia, pneumonia; acute intestinal diseases; allergic airway diseases; acute myocardial infarction and acute coronary syndrome; acute cerebrovascular accident, stroke; elevated blood pressure, hypertension; chronic ischemic heart disease, angina pectoris; cardiopsychoneurosis; migraine headache, migraine; heart rhythm disorder, arrhythmia; chronic upper respiratory tract diseases; chronic lung diseases, bronchitis; bronchial asthma; chronic gastrointestinal diseases; cholelithiasis and urolithiasis; chronic urinary tract diseases; chronic diseases of female sex organs; chronic joint diseases, arthritides; ocular hypertension, glaucoma; hay fever, grass pollen allergy,
- the information about the effect of environmental parameters on a body is displayed individually for each factor in the form of three conditions: extremely adverse parameters, adverse parameters, favorable parameters.

In contrast to the closest analog, the method and system according to the present invention allow including more parameters while maintaining high performance by the use of the system structure according to the present invention and an algorithm of its operation. In particular, the present invention uses an encoder to generate a single hash code comprising user and forecast data, thus, simplifying the correlation of parameters with the evaluation of the effect and accelerating the system operation by processing data in a single operation. The use of the hash coding provides convolution (correlation) of a full information set into a unique hash code, which unambiguously identifies all possible person medical problems, associated with the full parameter set of weather, geomagnetic background, and air quality according to a degree of their meteosensitivity.

BRIEF DESCRIPTION OF THE SEVERAL VIEWS OF THE DRAWINGS

The FIGURE is a schematic view of a diagram of a system for evaluation of the environmental effect on a user body.

DETAILED DESCRIPTION OF THE INVENTION

The claimed system for evaluation of the effect of environmental parameters includes a means (1) for inputting data of a computer device (2) user, a means (3) for determining or inputting a geolocation (a location) of the user, a processing unit (4), a weather server (5), external services for forecasting the weather and geomagnetic background (6) and air condition (7), an encoder (8), a decoder (9), a database (10) of dependencies of the functioning of human body systems on environmental parameters (weather, geomagnetic background and air), and a means (11) for displaying an effect of said parameters on the functioning of a person's body by each individual system (disease group).

The user computer device (2) (a terminal) can be a smartphone, a tablet, a PC, etc. configured to communicate data via the Internet (12). The means (1) for inputting user personal data can be implemented in the form of a software interface of the computer device (2). The means (3) for determining or inputting a geolocation can be an interface element for data input or a navigation module (GPS, Glonass, etc.) for automatically locating a user location which can be or can't be a component of the computer device (2).

The processing unit (4) is connected to the computer device (2) and controls the device. The weather server (5) is connected to the processing unit and is responsible for requesting and pre-processing data about a weather, geomagnetic background and air condition in a specific geolocation according to the information obtained from the external services (6) and (7). The encoder (8) is connected to the processing unit (4) and generates a hash code according to the user and forecast data. The decoder (9) is connected to the encoder (8) and maps the hash code received from the encoder having a database (10) storing a hash table of dependencies of the functioning of different human body systems on different weather, geomagnetic background and air parameters, and in case of a match it selects the information related to the information of the selected hash code and transforms it into a view ready to be displayed. The means (11) for displaying receives data from the decoder (9) and visualizes estimation results.

The method for multi-parameter evaluating the effect of weather, geomagnetic background and air condition parameters on the functioning of different human body systems is based on the usage of the following main environmental parameters:

For weather:
air temperature
atmospheric pressure,
air humidity,
wind direction and power,
precipitation type and rate,
atmospheric pressure dynamics for 12 hours,
UV-index (describing the level of ultraviolet solar radiation on the Earth's surface).

For air:
background air pollution,
presence of allergenic pollen in the air.

Based on analysis of results of biometeorology studies, it is defined following disease groups (or individual diseases) for human body, wherein the weather, air and geomagnetic background parameters may effect on their appearance and progression:

enhanced emotional lability, neurosis (influenced by barometric pressure value and dynamics, geomagnetic background), acute respiratory diseases (influenced by ambient temperature, barometric pressure value, humidity, the presence of rainfall);

tonsillitis, aggravation of chronic tonsillitis (influenced by ambient temperature, barometric pressure value);

acute pneumonia, pneumonia (influenced by ambient temperature, humidity, air quality index);

acute intestinal diseases (influenced by ambient temperature, barometric pressure value);

allergic airway diseases (influenced by barometric pressure value, humidity, air quality index);

acute myocardial infarction and acute coronary syndrome (influenced by barometric pressure value and dynamics, geomagnetic background, air quality index);

acute cerebrovascular accident, stroke (influenced by barometric pressure value and dynamics, geomagnetic background, air quality index);

elevated blood pressure, hypertension (influenced by ambient temperature, barometric pressure value and dynamics, air humidity, geomagnetic background, air quality index);

chronic ischemic heart disease, angina pectoris (influenced by ambient temperature, barometric pressure value and dynamics, geomagnetic background, air quality index);

cardiopsychoneurosis (influenced by barometric pressure value and dynamics, geomagnetic background);

a migraine headache, migraine (influenced by barometric pressure value and dynamics, geomagnetic background);

heart rhythm disorder, arrhythmia (influenced by barometric pressure value and dynamics, geomagnetic background);

chronic upper respiratory tract diseases (influenced by ambient temperature, humidity, the presence of rainfall, air quality index);

chronic lung diseases, bronchitis (influenced by ambient temperature, barometric pressure value and dynamics, humidity, the presence of rainfall, air quality index);

bronchial asthma (influenced by ambient temperature, barometric pressure value and dynamics, humidity, air quality index);

chronic gastrointestinal diseases (influenced by ambient temperature, barometric pressure value and dynamics);

cholelithiasis and urolithiasis (influenced by ambient temperature, barometric pressure value, the presence of rainfall);

chronic urinary tract diseases (influenced by ambient temperature, humidity, the presence of rainfall);

chronic diseases of female sex organs (influenced by ambient temperature, humidity, the presence of rainfall);

chronic joint diseases, arthritides (influenced by ambient temperature, barometric pressure dynamics, humidity, the presence of rainfall);

ocular hypertension, glaucoma (influenced by ambient temperature, barometric pressure value and dynamics, humidity);

hay fever, grass pollen allergy (influenced by flowering calender of different allergenic plants and herbs in a distribution area thereof, wind direction and strength, the presence of rainfall).

Preferably, all the values of the weather, geomagnetic background and air parameters are divided into ranges consisting of three groups:

increased values of parameters relative to normal values;
normal values of parameters;
decreased values of parameters relative to normal values.

Based on the data about the effect of the weather, geomagnetic background and air parameters on the functioning of different human body systems and three groups of parameter ranges, a hash table of dependencies of the functioning of different human body systems from values of weather and air parameters is created and is stored in a database (10). It should be noted, that particular dependencies of the effect of changing certain environmental parameters on a body condition are known to those skilled in the biometeorology so that this information is not described herein.

Correction factors may be introduced for the normal values of weather parameters, wherein said factors are associated with Earth's climate zones (the values for the normal weather parameters vary for different climate zones).

According to the method of the present invention, a user initiates by means of the computer device (2) reading and sending data about their location using the means (3) (for example, a GPS module of a smartphone). Furthermore, the user may input geolocation information manually. Furthermore, the user transmits personal data, including gender, age and, if necessary, a degree of meteosensitivity using an interactive interface (an input means 1). The personal data also can include additional parameters, for example, information about a susceptibility to certain diseases etc. The data received from the user containing personal and geolocation data is transmitted to a processing unit.

The processing unit (4) determines the climate zone at the user location and transmits this information about the user geolocation to a weather server (5), which requests forecast and/or current data about current weather conditions, geomagnetic background and air in the user location (or location of interest) from the external services (6) and (7). Then, an encoded signal from the weather server (5) comprising information about a weather forecast, geomagnetic background and air condition is transmitted to the processing unit (4).

The processing unit (4) transmits signals with the user and forecast data to an encoder (8) input. The encoder (8) generates a single hash code based on input signals, said code comprises user personal data, geolocation data and current weather, geomagnetic background and air parameters. Then, the hash code is transmitted to a decoder (9), which correlates, according to a signal (a command) from the processing unit (4), the received hash code with the database of dependencies of the functioning different human body systems from environmental parameters (weather, geomagnetic background and air parameters) according to the hash table.

Encoding results are transmitted to the means (11) for displaying an effect of current weather, geomagnetic background and air parameters on the functioning of different human body systems.

The principle of displaying the effect of the parameters may be based on displaying three conditions for each body system or disease group: extremely adverse parameters of weather, geomagnetic background and air; adverse parameters; favorable parameters.

EXAMPLE

A user inputs following parameters by means of the computer device:
gender: male;
age: over 36 years;
a degree of meteosensitivity: medium;

medical problems, associated with: hay fever and hypertension.

According to the geolocation data of the computer device, the user is in a 5th climate zone (normal values of weather parameters specific to this climate zone will be used based on this information).

Based on the user personal and biometeorology data, the following disease groups (or individual diseases) for a given person will be defined, wherein the weather, air and geomagnetic background parameters can impact appearance and progression of the diseases:

- enhanced emotional lability, neurosis;
- acute respiratory diseases;
- tonsillitis, aggravation of chronic tonsillitis;
- acute pneumonia, pneumonia;
- acute intestinal diseases;
- allergic airway diseases;
- acute myocardial infarction and acute coronary syndrome;
- acute cerebrovascular accident, stroke;
- elevated blood pressure, hypertension;
- chronic ischemic heart disease, angina pectoris;
- cardiopsychoneurosis;
- a migraine headache, migraine;
- heart rhythm disorder, arrhythmia;
- chronic upper respiratory tract diseases;
- chronic lung diseases, bronchitis;
- bronchial asthma;
- chronic gastrointestinal diseases;
- cholelithiasis and urolithiasis;
- chronic urinary tract diseases;
- chronic joint diseases, arthritides,
- ocular hypertension, glaucoma;
- hay fever, grass pollen allergy.

Upon request of weather and air condition data, the following information was obtained:

- air temperature—28,
- atmospheric pressure—760 mm Hg,
- humidity—71%,
- atmospheric pressure dynamics for last 12 hours—0,
- rainfalls,
- geomagnetic background—disturbed,
- UV-index—6,
- a high pollen concentration of weeds (nettle, wormwood etc.) and fungal spores (*cladosporium, alternaria*) in a user geolocation in the 5th climate zone,
- an AQI (air quality index)—56.82756.

The user data and received data about the weather forecast, geomagnetic background and air condition are transmitted to the encoder which convolves (transforms) it into a hash code. Thereafter, upon a processing unit signal, the hash code is transmitted to the decoder. Then, according to transmitted hash code a record is retrieved from the database, said record associates the hash code with potential risks of the functioning of different human body systems based on a user's degree of meteosensitivity.

With respect to the aforementioned user data and data received from the weather server, the user obtains the following information which can be displayed by the means for displaying information:

Enhanced emotional lability, neurosis (influenced by geomagnetic background)—a "yellow" condition indicator, recommendations associated with the health condition include the following:

"Enhanced emotional lability, low mood, decreased performance and even a headache and pain in the heart area can be expected today. Compliance with the work and rest schedule together with a good sleep may help to overcome said negative effects. Take a walk in the open air before going to bed. In case of prescribed sedative, make sure you take it carefully."

Acute respiratory diseases (influenced by ambient temperature, humidity, the presence of rainfall)—a "yellow" condition indicator, recommendations associated with the health condition include the following: "The weather promotes the development of an acute respiratory disease. Symptoms can include a high temperature, cough, rhinitis. As a precaution to not to get sick, avoid contacting people with said symptoms, get dressed according to the weather and keep your feet dry."

Tonsillitis, aggravation of chronic tonsillitis—a "green" condition indicator, recommendations associated with the health condition include the following: "Today the risk of getting acute tonsillitis or aggravation of chronic tonsillitis is low. However, be always careful with cold drinks and ice cream!"

Acute pneumonia, pneumonia—a "green" condition indicator, recommendations associated with the health condition include the following: "Today's weather doesn't promote acute pneumonia and bronchitis. Make a healthy and active lifestyle!"

Acute intestinal diseases—a "green" condition indicator, recommendations associated with the health condition include the following: "Today the risk of appearance of acute intestinal diseases is low. But you always have to maintain personal hygiene!"

Allergic airway diseases (influenced by humidity, air quality index)—a "yellow" condition indicator, recommendations associated with the health condition include the following: "Today's weather is not favorable for people having allergic airway diseases. It is better to mop in your room. It is recommended to wash your nose with still mineral water before going outdoors. For people having an allergy, it is better to avoid eating chocolate, citrus fruits, and other allergenic products."

Acute myocardial infarction and acute coronary syndrome (influenced by geomagnetic background, air quality index)—a "yellow" condition indicator, recommendations associated with the health condition include the following: "The risk of development of acute coronary syndrome, including acute myocardial infarction, is increased. It is recommended to avoid superfluous stresses and emotions. Take the medical preparations enhancing heart performance, if prescribed by the physician. In the case of spasm of intense pain in a chest region or sudden dyspnea, immediately seek medical help."

Acute cerebrovascular accident, stroke (influenced by geomagnetic background, air quality index)—a "yellow" condition indicator, recommendations associated with the health condition include the following: "The risk of development of acute cerebrovascular accident is increased today. Continuously monitor your blood pressure level. Try to avoid stresses and superfluous emotions. Carefully take the medical preparations, in particular, those that effect on blood pressure and blood coagulability, if prescribed."

Elevated blood pressure, hypertension (influenced by air humidity, geomagnetic background, air quality index)—a "yellow" condition indicator, recommendations associated with the health condition include the following: "The increased risk of decompensation of arterial hypertension is increased today. If you have such problem, you should monitor your pressure level at least twice a day. Try to avoid superfluous nerves and stresses, avoid overeating and limit salt intake to 2 g a day. If you are prescribed with medical preparations which reduce blood pressure, don't forget to take it carefully".

Chronic ischemic heart disease, angina pectoris; (influenced by geomagnetic background, air quality index)—a "yellow" condition indicator, recommendations associated with the health condition include the following: "The weather increases the frequency of anginal attacks and promotes aggravation of chronic ischemic heart disease. If you have such disease try to avoid excessive physical activities. Also, avoid overeating. Take all medical preparations prescribed by a physician and keep nitroglycerin at hand.";

Cardiopsychoneurosis (influenced by geomagnetic background)—a "yellow" condition indicator, recommendations associated with the health condition include the following: "The risk of feeling unwell for people having cardiopsychoneurosis is increased today. It can take forms of fluctuations of blood pressure, accompanied by weakness, headache, a pain in the heart area and other clinical implications of this disease. You should take at least 2 glasses of liquid more than usually. Try to comply a work and rest schedule."

A migraine headache, migraine (influenced by geomagnetic background)—a "yellow" condition indicator, recommendations associated with the health condition include the following: "The risk of development of migraine attack is increased. To prevent it try to get enough sleep, avoid planning serious business for today and limit your physical activity. Follow moderate eating: avoid fatty and fried food, instead eat fish and sea fruits. Also, drink more liquid, such as mineral water and juices. If you have such problem, keep medical preparations for headaches at hand. The most efficient way is to take the medical preparations at the beginning of the attack, don't stand the pain."

Heart rhythm disorder, arrhythmia (influenced by geomagnetic background)—a "yellow" condition indicator, recommendations associated with the health condition include the following: "The risk of development of cardiac arrhythmia is increased today, such as improper heart performance and episodes of the improper or fast heartbeat. If you have such problem, keep medical preparations which help you in such situations at hand. If they don't have a positive effect, immediately seek a physician or call an ambulance."

Chronic upper respiratory tract diseases (influenced by humidity, the presence of rainfall, air quality index)—a "yellow" condition indicator, recommendations associated with the health condition include the following: "The risk of development of aggravation of chronic upper respiratory tract diseases is increased today. It can be accompanied by appearance or aggravation of dry heavy cough. To prevent aggravation, get dressed according to the weather and keep dry your clothes and in particular your footwear. Avoid overloading your vocal cords."

Chronic lung diseases, bronchitis—a "green" condition indicator, recommendations associated with the health condition include the following: "It is a favorable weather for people having chronic bronchitis. We wish you a good day and light breathing!";

Bronchial asthma—a "green" condition indicator, recommendations associated with the health condition include the following: "It is a favorable weather for people having bronchial asthma. We wish you a good day and light and free breathing!"

Chronic gastrointestinal diseases—a "green" condition indicator, recommendations associated with the health condition include the following: "It is a favorable weather for people having chronic gastrointestinal diseases. We wish you a nice meal!"

Cholelithiasis and urolithiasis—a "green" condition indicator, recommendations associated with the health condition include the following: "It is a favorable weather for people having kidney stones and gallstones. We wish you a good day and success in all undertakings!"

Chronic urinary tract diseases (influenced by ambient temperature, humidity, the presence of rainfall)—a "yellow" condition indicator, recommendations associated with the health condition include the following: "The risk of development of aggravation of chronic inflammatory kidney and urinary tract diseases is increased today. To prevent it keep your waist area warm. Pay attention to keep dry your clothes and, in particular, footwear. Keep your legs warm."

Chronic joint diseases, arthritides (influenced by ambient temperature, humidity, the presence of rainfall)—a "yellow" condition indicator, recommendations associated with the health condition include the following: "The risk of aggravation of spine and joint diseases, as well as pains therein today. Try to keep your joints warm and avoid excessive physical activities. Keep your legs always dry and warm. Try not to overload affected joints. You can take anti-inflammatory medicine in ointment and application forms.";

Ocular hypertension, glaucoma—a "green" condition indicator, recommendations associated with the health condition include the following: "It is a favorable weather for people having ocular hypertension. We wish you to see the world in all the diversity of its colors!"

Hay fever, grass pollen allergy (influenced by flowering calendar of different allergenic plants and herbs in a distribution area thereof, wind direction and strength, the presence of rainfall)—a "red" condition indicator, recommendations associated with the health condition include the following: "Attention! There is a high pollen concentration of nettle, wormwood, meadow grasses, mushroom spores in the air, which may adversely impact your health. Rainfalls reduce the pollen concentration in the air. Avoid eating products which can cause a cross-feeding response, in particular, during a period of allergenic plant flowering. Regularly wash your nasal cavity to wash out allergens, in particular, after getting off the street. Where possible, you should go to another climate zone, where allergenic plants flower during another time period or where they are absent. To relief the symptoms of allergy take anti-allergic medicine according to the physician prescription."

Therefore, a user may operatively receive relevant information about the effect of the environmental parameters on the functioning of separate body systems.

The disclosed system can be embodied as an application for a mobile device or a personal computer.

The invention claimed is:

1. A method for multi-parameter evaluating an effect of environmental parameters on functioning of human body systems of a user with a computer device, the method comprising the steps of:
   inputting personal data of the user to a computer device, said computer device being comprised of a display, said personal data being comprised of gender, age, and degree of meteosensitivity;
   inputting geolocation data of the user to said computer device;
   transmitting said personal data and said geolocation data from said computer device to a processing unit;
   requesting environmental forecast data from a weather server by said processing unit, said environmental forecast data being comprised of: forecast data about weather, geomagnetic background, and air condition, said environmental forecast data corresponding to said geolocation data;
   transmitting said environmental forecast data from said weather server to said processing unit;
   transmitting said personal data and said environmental forecast data to an encoder so as to generate a single hash code containing said personal data and said environmental forecast data;
   transmitting said single hash code to a decoder;
   correlating said single hash code with at least one dependency of functioning of human body systems from a database of dependencies of a functioning of human body systems based on said environmental forecast data so as to form correlated data;
   transmitting said correlated data to said display of said computer device; and
   displaying said correlated data so as to provide information about an effect of environmental parameters on functioning of human body systems of the user.

2. The method of claim 1, wherein the step of inputting geolocation data of the user to said computer device is selected from at least one of a group consisting of: specifying said geolocation data, and determining said geolocation data, and
   wherein said computer device is further comprised of a navigation module, and
   wherein the step of determining said geolocation data is comprised of determining said geolocation data with said navigation module.

3. The method of claim 1, wherein said computer device is further comprised of an interface, and wherein the step of inputting said personal data is comprised of inputting said personal data by said interface.

4. The method of claim 1, wherein said forecast data about weather is comprised of at least one of a group consisting of: an air temperature, atmospheric pressure, air humidity, wind direction, wind strength, rainfall type, rainfall intensity, atmospheric pressure dynamics for 12 hours, and an ultraviolet index.

5. The method of claim 1, wherein said air condition is comprised of at least one of a group consisting of: a background air pollution, and presence of allergenic pollen in air.

6. The method of claim 1, further comprising the step of: using external services by said weather server for forecasting weather, geomagnetic background, and air condition in order to determine said forecast data about weather.

7. The method of claim 1, wherein said database of dependencies of functioning of human body systems based on said environmental forecast data is comprised of at least one factor related to disease groups, and wherein said disease groups are comprised of at least one of a group consisting of:
   enhanced emotional lability, neurosis,
   acute respiratory diseases,
   tonsillitis, aggravation of chronic tonsillitis,
   acute pneumonia, pneumonia,
   acute intestinal diseases,
   allergic airway diseases,
   acute myocardial infarction and acute coronary syndrome,
   acute cerebrovascular accident, stroke,
   elevated blood pressure, hypertension,
   chronic ischemic heart disease, angina pectoris,
   cardiopsychoneurosis,
   a migraine headache, migraine,
   heart rhythm disorder, arrhythmia,
   chronic upper respiratory tract diseases,
   chronic lung diseases, bronchitis,
   bronchial asthma,
   chronic gastrointestinal diseases,
   cholelithiasis and urolithiasis,
   chronic urinary tract diseases,
   chronic diseases of female sex organs,
   chronic joint diseases, arthritides,
   ocular hypertension, glaucoma, and
   hay fever, grass pollen allergy.

8. The method of claim 7, wherein the step of displaying said correlated data so as to provide information about an effect of environmental parameters on functioning of human body systems of the user is comprised of:
   independently displaying information about a corresponding effect of environmental parameters for each factor, each corresponding effect being comprised of three conditions, said three conditions being extremely adverse parameters, adverse parameters, and favorable parameters.

9. A system of multi-parameter evaluation of an effect of environmental parameters on functioning of human body systems of a user, comprising:
   a computer device being comprised of:
      a means for inputting personal data of the user into said computer device, said personal data being comprised of gender, age, and degree of meteosensitivity; and
      a means for inputting geolocation data of the user, to the computer device;
   a processing unit being in communication with said computer device so as to receive said personal data and said geolocation data from said computer device;
   a weather server being connected to said processing unit and having environmental forecast data from external services for forecasting weather, geomagnetic background, and air condition, said environmental forecast data being comprised of forecast data about weather, geomagnetic background, and air condition, said environmental forecast data corresponding to said geolocation data;
   an encoder connected to said processing unit so as to generate a single hash code containing said personal data and said environmental forecast data;
   a decoder connected to said encoder so as to correlate said single hash code with at least one dependency of functioning of human body systems from a database of dependencies of functioning of human body systems based on said environmental forecast data so as to form correlated data, said database of dependencies being connected to said decoder and being comprised of a hash table of dependencies of functioning of human body systems; and a means for displaying said correlated data so as to provide information about an effect of environmental parameters on functioning of human body systems of the user.

10. The system of claim 9, wherein said effect of environmental parameter on functioning of human body systems is comprised of three conditions, said three condition being: extremely adverse parameters, adverse parameters, and favorable parameters.

11. The system of claim 9, wherein said means for inputting said geolocation data is comprised of a navigation module.

12. The system of claim 9, wherein said means for inputting said geolocation data is comprised of a software interface so as to input parameters of said geolocation data.

* * * * *